United States Patent
Grimshaw et al.

(10) Patent No.: US 7,425,341 B1
(45) Date of Patent: Sep. 16, 2008

(54) RAPIDLY DISINTEGRABLE TABLETS

(75) Inventors: Michael N. Grimshaw, St. Louis, MO (US); Donald J. Barbieri, Fenton, MO (US); Louise M. Vizzini, St. John, MO (US); Steve F. Marsh, St. Charles, MO (US)

(73) Assignee: K.V. Pharmaceutical Company, St. Louis, MO (US)

( * ) Notice: Subject to any disclaimer, the term of this patent is extended or adjusted under 35 U.S.C. 154(b) by 0 days.

(21) Appl. No.: 11/853,355

(22) Filed: Sep. 11, 2007

Related U.S. Application Data

(62) Division of application No. 10/929,856, filed on Aug. 30, 2004, now Pat. No. 7,282,217.

(60) Provisional application No. 60/498,948, filed on Aug. 29, 2003.

(51) Int. Cl.
  *A61K 9/36* (2006.01)
  *A61K 47/00* (2006.01)
  *A66K 9/26* (2006.01)

(52) U.S. Cl. .................. 424/479; 424/470; 424/439

(58) Field of Classification Search ............. 424/464, 424/465, 479, 52, 439, 440, 470
See application file for complete search history.

(56) References Cited

U.S. PATENT DOCUMENTS

| | | |
|---|---|---|
| 1,450,865 A | 4/1923 | Pelc |
| 3,438,787 A | 4/1969 | DuRoss |
| 3,560,225 A | 2/1971 | Wonsiewicz et al. |
| 3,639,169 A | 2/1972 | Broeg et al. |
| 3,800,045 A | 3/1974 | Brucker et al. |
| 3,809,756 A | 5/1974 | Bush et al. |
| 3,873,694 A | 3/1975 | Kanig |
| 3,962,417 A | 6/1976 | Howell |
| 4,013,775 A | 3/1977 | Nelson et al. |
| 4,072,535 A | 2/1978 | Short et al. |
| 4,305,502 A | 12/1981 | Gregory et al. |
| 4,327,076 A | 4/1982 | Puglia et al. |
| 4,327,077 A | 4/1982 | Puglia et al. |
| 4,371,516 A | 2/1983 | Gregory et al. |
| 4,438,263 A | 3/1984 | Morse |

(Continued)

FOREIGN PATENT DOCUMENTS

EP      0 331 404 A2      9/1989

(Continued)

OTHER PUBLICATIONS

Armstrong et al., "Mannitol," *Handbook of Pharmaceutical Excipients*, 294-298 (1994).

(Continued)

*Primary Examiner*—Sharon E. Kennedy
(74) *Attorney, Agent, or Firm*—Leydig, Voit & Mayer, Ltd

(57) ABSTRACT

The invention provides a rapidly disintegrating tablet comprising an active ingredient, a water soluble, directly compressible carbohydrate, and a water soluble, directly compressible filler. Also provided is a method of producing a rapidly disintegrating tablet, which method comprises wet granulating a mixture comprising a directly compressible, water soluble carbohydrate, a directly compressible, water insoluble filler, a beneficial ingredient, and a solvent, and compressing the granulate to produce the tablet.

28 Claims, 1 Drawing Sheet

U.S. PATENT DOCUMENTS

| | | |
|---|---|---|
| 4,597,959 A | 7/1986 | Barr |
| 4,613,497 A | 9/1986 | Chavkin |
| 4,639,368 A | 1/1987 | Niazi et al. |
| 4,684,534 A | 8/1987 | Valentine |
| 4,687,662 A | 8/1987 | Schobel |
| 4,693,750 A | 9/1987 | Bauer et al. |
| 4,710,390 A | 12/1987 | Schumacher et al. |
| 4,714,620 A | 12/1987 | Bunick et al. |
| 4,753,792 A | 6/1988 | Aberg |
| 4,754,597 A | 7/1988 | Buxton et al. |
| 4,806,358 A | 2/1989 | Khan et al. |
| 4,829,056 A | 5/1989 | Sugden |
| 4,855,326 A | 8/1989 | Fuisz |
| 4,866,046 A | 9/1989 | Amer |
| 4,874,614 A | 10/1989 | Becker |
| 4,940,588 A | 7/1990 | Sparks et al. |
| 4,946,684 A | 8/1990 | Blank et al. |
| 4,946,685 A | 8/1990 | Edgren et al. |
| 4,970,236 A | 11/1990 | Ziggiotti et al. |
| 4,980,169 A | 12/1990 | Oppenheimer et al. |
| 5,028,633 A | 7/1991 | Ohno et al. |
| 5,055,306 A | 10/1991 | Barry et al. |
| 5,057,319 A | 10/1991 | Gottwald et al. |
| 5,064,650 A | 11/1991 | Lew |
| 5,073,374 A | 12/1991 | McCarty |
| 5,132,114 A | 7/1992 | Stanley et al. |
| 5,178,878 A | 1/1993 | Wehling et al. |
| 5,202,128 A | 4/1993 | Morella et al. |
| 5,204,115 A | 4/1993 | Olinger et al. |
| 5,215,741 A | 6/1993 | Young et al. |
| 5,215,755 A | 6/1993 | Roche et al. |
| 5,217,965 A | 6/1993 | Oshlack et al. |
| 5,219,574 A | 6/1993 | Wehling et al. |
| 5,225,197 A | 7/1993 | Bolt et al. |
| 5,260,072 A | 11/1993 | Roche et al. |
| 5,288,497 A | 2/1994 | Stanley et al. |
| 5,298,261 A | 3/1994 | Pebley et al. |
| 5,320,855 A | 6/1994 | Roche et al. |
| 5,330,766 A | 7/1994 | Morella et al. |
| 5,352,448 A | 10/1994 | Bowersock et al. |
| 5,376,692 A | 12/1994 | Park et al. |
| 5,378,474 A | 1/1995 | Morella et al. |
| 5,382,437 A | 1/1995 | Ecanow |
| 5,401,514 A | 3/1995 | Juch et al. |
| 5,464,632 A | 11/1995 | Cousin et al. |
| 5,501,861 A | 3/1996 | Makino et al. |
| 5,503,846 A | 4/1996 | Wehling et al. |
| 5,505,982 A | 4/1996 | Krawczyk et al. |
| 5,529,789 A | 6/1996 | Lo |
| 5,536,526 A | 7/1996 | Virtanen et al. |
| 5,556,639 A | 9/1996 | Fielden |
| 5,558,880 A | 9/1996 | Gole et al. |
| 5,563,210 A | 10/1996 | Donatelli et al. |
| 5,567,439 A | 10/1996 | Myers et al. |
| 5,573,777 A * | 11/1996 | Serpelloni et al. ............ 424/440 |
| 5,576,014 A | 11/1996 | Mizumoto et al. |
| 5,587,180 A | 12/1996 | Allen, Jr. et al. |
| 5,595,761 A | 1/1997 | Allen, Jr. et al. |
| 5,607,697 A | 3/1997 | Alkire et al. |
| 5,609,883 A | 3/1997 | Valentine et al. |
| 5,622,719 A | 4/1997 | Myers et al. |
| 5,631,022 A | 5/1997 | Mandel et al. |
| 5,631,023 A | 5/1997 | Kearney et al. |
| 5,635,210 A | 6/1997 | Allen, Jr. et al. |
| 5,637,313 A | 6/1997 | Chau et al. |
| 5,648,093 A | 7/1997 | Gole et al. |
| 5,654,003 A | 8/1997 | Fuisz et al. |
| 5,660,860 A | 8/1997 | Fielden |
| 5,674,495 A | 10/1997 | Bowersock et al. |
| 5,698,226 A | 12/1997 | Fielden |
| 5,707,646 A | 1/1998 | Yajima et al. |
| 5,720,974 A | 2/1998 | Makino et al. |
| 5,723,143 A | 3/1998 | Jacques et al. |
| 5,728,400 A | 3/1998 | Battist et al. |
| 5,750,585 A | 5/1998 | Park et al. |
| 5,762,961 A | 6/1998 | Roser et al. |
| 5,776,491 A | 7/1998 | Allen, Jr. et al. |
| 5,785,989 A | 7/1998 | Stanley et al. |
| 5,807,518 A | 9/1998 | Menard et al. |
| 5,807,576 A | 9/1998 | Allen, Jr. et al. |
| 5,807,578 A | 9/1998 | Acosta-Cuello et al. |
| 5,830,456 A | 11/1998 | Cummins |
| 5,837,285 A | 11/1998 | Nakamichi et al. |
| 5,840,334 A | 11/1998 | Raiden et al. |
| 5,846,526 A | 12/1998 | Cummins |
| 5,846,568 A | 12/1998 | Olinger et al. |
| 5,851,552 A | 12/1998 | Myers et al. |
| 5,851,553 A | 12/1998 | Myers et al. |
| 5,853,758 A | 12/1998 | Lo |
| 5,853,762 A | 12/1998 | Myers et al. |
| 5,866,163 A | 2/1999 | Myers et al. |
| 5,869,098 A | 2/1999 | Misra et al. |
| 5,871,781 A | 2/1999 | Myers et al. |
| 5,876,759 A | 3/1999 | Gowan, Jr. |
| 5,882,640 A | 3/1999 | Cummins |
| 5,895,664 A | 4/1999 | Cherukuri et al. |
| 5,902,606 A | 5/1999 | Wunderlich et al. |
| 5,965,162 A | 10/1999 | Fuisz et al. |
| 5,968,221 A | 10/1999 | Blais |
| 5,972,383 A | 10/1999 | Gibson et al. |
| 5,980,941 A | 11/1999 | Raiden et al. |
| 6,013,855 A | 1/2000 | McPherson et al. |
| 6,018,033 A | 1/2000 | Chen et al. |
| 6,020,002 A | 2/2000 | Myers et al. |
| 6,024,981 A * | 2/2000 | Khankari et al. ............ 424/464 |
| 6,071,539 A | 6/2000 | Robinson et al. |
| 6,083,430 A | 7/2000 | Fuisz et al. |
| 6,083,531 A | 7/2000 | Humbert-Droz et al. |
| 6,103,219 A | 8/2000 | Sherwood et al. |
| 6,139,865 A | 10/2000 | Friend et al. |
| 6,143,324 A | 11/2000 | Michaud et al. |
| 6,156,771 A | 12/2000 | Rubin et al. |
| 6,165,512 A | 12/2000 | Mezaache et al. |
| 6,194,000 B1 | 2/2001 | Smith et al. |
| 6,221,392 B1 | 4/2001 | Khankari et al. |
| 6,270,804 B1 | 8/2001 | Getz et al. |
| 6,271,278 B1 | 8/2001 | Park et al. |
| 6,280,769 B1 | 8/2001 | D'Amelia et al. |
| 6,287,596 B1 | 9/2001 | Murakami et al. |
| 6,294,192 B1 | 9/2001 | Patel et al. |
| 6,316,029 B1 | 11/2001 | Jain et al. |
| 6,372,218 B1 | 4/2002 | Cummins |
| 6,375,982 B1 | 4/2002 | Cherukuri |
| 6,406,717 B2 | 6/2002 | Cherukuri |
| 6,465,009 B1 | 10/2002 | Liu et al. |
| 6,471,945 B2 | 10/2002 | Luo et al. |
| 6,475,510 B1 * | 11/2002 | Venkatesh et al. ............ 424/441 |
| 6,479,071 B2 | 11/2002 | Holme et al. |
| 6,488,961 B1 | 12/2002 | Robinson et al. |
| 6,511,679 B2 | 1/2003 | D'Amelia et al. |
| 6,555,145 B1 | 4/2003 | Cherukuri |
| 6,592,902 B2 * | 7/2003 | Thosar et al. ............... 424/489 |
| 6,599,627 B2 | 7/2003 | Yeo et al. |
| 2001/0018074 A1 | 8/2001 | Napper et al. |
| 2002/0012680 A1 | 1/2002 | Patel et al. |
| 2002/0031552 A1 | 3/2002 | McTeigue et al. |
| 2002/0044960 A1 | 4/2002 | Cherukuri |
| 2002/0071857 A1 | 6/2002 | Karali et al. |
| 2002/0071864 A1 | 6/2002 | Kim et al. |
| 2002/0082680 A1 | 6/2002 | Shanley et al. |
| 2002/0119196 A1 | 8/2002 | Parikh et al. |
| 2002/0142045 A1 | 10/2002 | Kararli et al. |
| 2002/0160109 A1 | 10/2002 | Yeo et al. |
| 2002/0165392 A1 | 11/2002 | Kim et al. |

| | | | |
|---|---|---|---|
| 2002/0168386 | A1 | 11/2002 | Gergely et al. |
| 2002/0187188 | A1 | 12/2002 | Cherukuri |
| 2002/0197321 | A1 | 12/2002 | Seager |
| 2003/0022912 | A1 | 1/2003 | Martino et al. |
| 2003/0031715 | A1 | 2/2003 | Park et al. |
| 2003/0049316 | A1 | 3/2003 | Robinson et al. |
| 2003/0170310 | A1* | 9/2003 | Wadhwa ............... 424/486 |

FOREIGN PATENT DOCUMENTS

| | | |
|---|---|---|
| JP | 36 0174782 A | 9/1985 |
| JP | 36 2006674 A | 1/1987 |
| JP | 36 2006675 A | 1/1987 |
| JP | 36 3059897 A | 3/1988 |
| JP | 36 3084497 A | 4/1988 |
| JP | 36 3087991 A | 4/1988 |
| JP | 40 1124383 A | 5/1989 |
| JP | 40 1273597 A | 11/1989 |
| WO | WO 87/04710 A1 | 8/1987 |
| WO | WO 94/02170 A1 | 2/1994 |
| WO | WO 96/03147 A1 | 2/1996 |
| WO | WO 98/05269 A1 | 2/1998 |
| WO | WO 98/51408 A1 | 11/1998 |
| WO | WO 98/51694 A2 | 11/1998 |
| WO | WO 02/30466 A2 | 4/2002 |
| WO | WO 03/015664 A1 | 2/2003 |
| WO | WO 03/053325 A2 | 7/2003 |
| WO | WO 2004/047810 A1 | 6/2004 |

OTHER PUBLICATIONS

Dallavalle, "Particle-Size Determination," *Micromeritics*, 113-114 (Copyright, 1943, 1948).

Ethex Corporation, "KV Pharmaceutical Launches First Product Utilizing Proprietary OraQuick Delivery System," *News & Events*, http://www.ethex.com/news (accessed Jan. 15, 2003).

Ghanem et al., "Mechanical and Physical Properties of Sulphamethoxazole-Mannitol Solid Disperson in Tablet Form," *Acta Pharmaceutica Fennica*, 95, 167-172 (1986).

Gorman et al., "An Evaluation of Croscarmellose as a Tablet Disintegrant in Direct Compression Systems," *Drug Development and Industrial Pharmacy*, 8 (3), 397-410 (1982).

Guyot-Hermann et al., "Gamma Sorbitol as a Diluent in Tablets," *Drug Development and Industrial Pharmacy*, 11 (2&3), 551-564 (1985).

Molokhia et al., "Aging of Tablets Prepared by Direct Compression of Bases with Different Moisture Content," *Drug Development and Industrial Pharmacy*, 13 (9-11), 1933-1946 (1987).

Park, "Superporous Hydrogels for Pharmaceutical & Other Applications," *Drug Delivery Technology*, http://www.drugdeliverytech.com (accessed Dec. 18, 2003).

Phipps, "Purdue Research Park company makes melt-in-your-mouth meds," *Purdue News*, http://news.uns.purdue.edu (assessed Aug. 9, 2004).

Schwarz Pharma, "Helping IBS Patients Get Back on Track-FAST," *NuLev*, http://www.nulev.com (accessed Oct. 11, 2002).

Cima, "NuLev (hyoscyamine sulfate orally disintegrating tables)," Jul. 2000.

Shin et al., "Preparation of fast-dissolving tablet having a porous structure," AAPS Pharm Sci, . 3 (3), (2001) (abstract).

Spi Pharma, "Mannogem™ EZ Spray Dried Mannitol," *Technical Bulletin*, 122.

Szabo-Revesz et al., "Microcrystal Cellulose Prepared Tablets Examination," *Pharm. Ind.*, 50 (8), 981-983 (1988).

Niro Pharma Systems, "Current Issues and troubleshooting Fluid Bed Granulation," Pharmceutical Technology Europe, May 1998.

Wambolt et al., "Comparison of Two Microcrystalline Cellulose Brands for the Direct Compression of Hydrochlorothiazide Tablets," *Pharm. Ind.*, 55 (11), 1046-1051 (1993).

Westermarck et al., "Microcrystallline cellulose and its microstructure in pharmaceutical processing," *European Journal of Pharmaceutics and Biopharmaceutics*, 48, 199-206 (1999).

Debord et al., "Study of Different Crystalline Forms of Mannitol: Comparative Behaviour Under Compression," *Drug Development and Industrial Pharmacy*, 13 (9-11), 1533-1546 (1987).

Fung et al., "Development of a Stable Sublingual Nitroglycerin Tablet II: Formulation and Evaluation of Tablets Containing Povidone," *J. Pharm. Sciences*, 65 (4), 558-560 (1976).

Kanig, "Properties of Fused Mannitol in Compressed Tablets," *J. Pharm. Sciences*, 53(2), 188-192 (1964).

Lagas et al., "Sublingual Nitroglycerin," *Pharmaceutisch Weekblad Scientific Edition*, 10, 246-253 (1988).

Ward et al., "Dissolution and Compatibility Considerations for the Use of Mannitol in Solid Dosage Forms," *J. Pharm. Sciences*, 58 (12), 1464-1467 (1969).

* cited by examiner

RAPIDLY DISINTEGRABLE TABLETS

CROSS-REFERENCE TO RELATED PATENT APPLICATIONS

This patent application, is a division of U.S. patent application Ser. No. 10/929,856, filed Aug. 30, 2004, which claims the benefit of U.S. Provisional Patent Application No. 60/498,948, filed Aug. 29, 2003.

FIELD OF THE INVENTION

This invention pertains to rapidly disintegrable tablets.

BACKGROUND OF THE INVENTION

Rapidly disintegrating tablets are convenient delivery systems, which are designed to disintegrate rapidly upon contact with a fluid medium, which is typically an aqueous fluid medium. Orally disintegrating tablets are a class of rapidly disintegrating tablets, which are convenient oral delivery systems designed to disintegrate rapidly upon contact with aqueous fluids, e.g., water or saliva, to form a dispersion, which can be swallowed easily. Orally disintegrating tablets are particularly advantageous for patients, e.g., pediatric or aged patients, having difficulty swallowing conventional tablets or capsules, or for individuals who may not have difficulty swallowing, but may have an aversion to swallowing conventional tablets or capsules. Orally disintegrating tablets also are convenient under circumstances in which taking an oral dosage form with water may be inconvenient (e.g., while working or traveling).

Conventional rapidly disintegrating tablets are typically formed by compression (e.g., in a tablet press). It is desirable for such tablets to have sufficiently high hardness and sufficiently low friability to provide structural stability for transportation and storage. Low friability (which is measured based on the percent tablet weight loss after a certain number of revolutions in a friabilator) is desirable in that it is generally indicative of high tablet strength. High porosity of the tablet structure also is desirable in that it allows fluids (e.g., aqueous or bodily fluids, e.g., water or saliva) to be drawn or "wicked" from the external environment and into the interstices of the tablet structure, thereby promoting rapid and effective disintegration.

Rapidly disintegrating tablets have been described in U.S. Pat. No. 5,464,632 (Cousin et al.), which describes a tablet prepared by dry blending an active ingredient with a granulated carbohydrate, to form a composition, which is compressed, to form the tablet. Rapidly disintegrating tablets also have been described in U.S. Pat. No. 6,316,029 (Jain et al.), which describes a tablet prepared by compressing a blend of ingredients into a tablet. However, the process of forming the tablet described by Jain et al. requires relatively high compression forces (e.g., from 700 lbs. to 3800 lbs.). The high compression forces can result in a reduction in tablet porosity due to collapse of the void spaces during compression, thereby sacrificing the disintegration properties of the tablet.

As such, there exists a need for a conventional rapidly disintegrating tablet having sufficiently low friability and sufficiently high hardness, while maintaining high porosity of the tablet structure. The invention provides such a tablet. These and other advantages of the invention, as well as additional inventive features, will be apparent from the description of the invention provided herein.

BRIEF SUMMARY OF THE INVENTION

The present invention provides a compressed rapidly disintegrating tablet comprising a beneficial ingredient, which is incorporated into a matrix comprising a water soluble, directly compressible carbohydrate, and a water insoluble, directly compressible filler. The tablet of the present invention has low friability (e.g., less than about 1.5%), high porosity (e.g., from about 15% to about 45%), and disintegrates rapidly in water (e.g., from within about 2 seconds to within about 120 seconds).

The present invention further provides a method of producing a rapidly disintegrating tablet. The method preferably comprises wet granulating a water soluble carbohydrate and a water insoluble filler in the presence of a beneficial ingredient and a solvent, to form a wet granulate. The wet granulate is dried, to produce a dry granulate comprising the beneficial ingredient, the water soluble carbohydrate and the water insoluble filler, and compressed to produce a rapidly disintegrating tablet. The wet granulate and/or dry granulate typically is blended with other ingredients prior to compression.

DETAILED DESCRIPTION OF THE INVENTION

Figure 1:
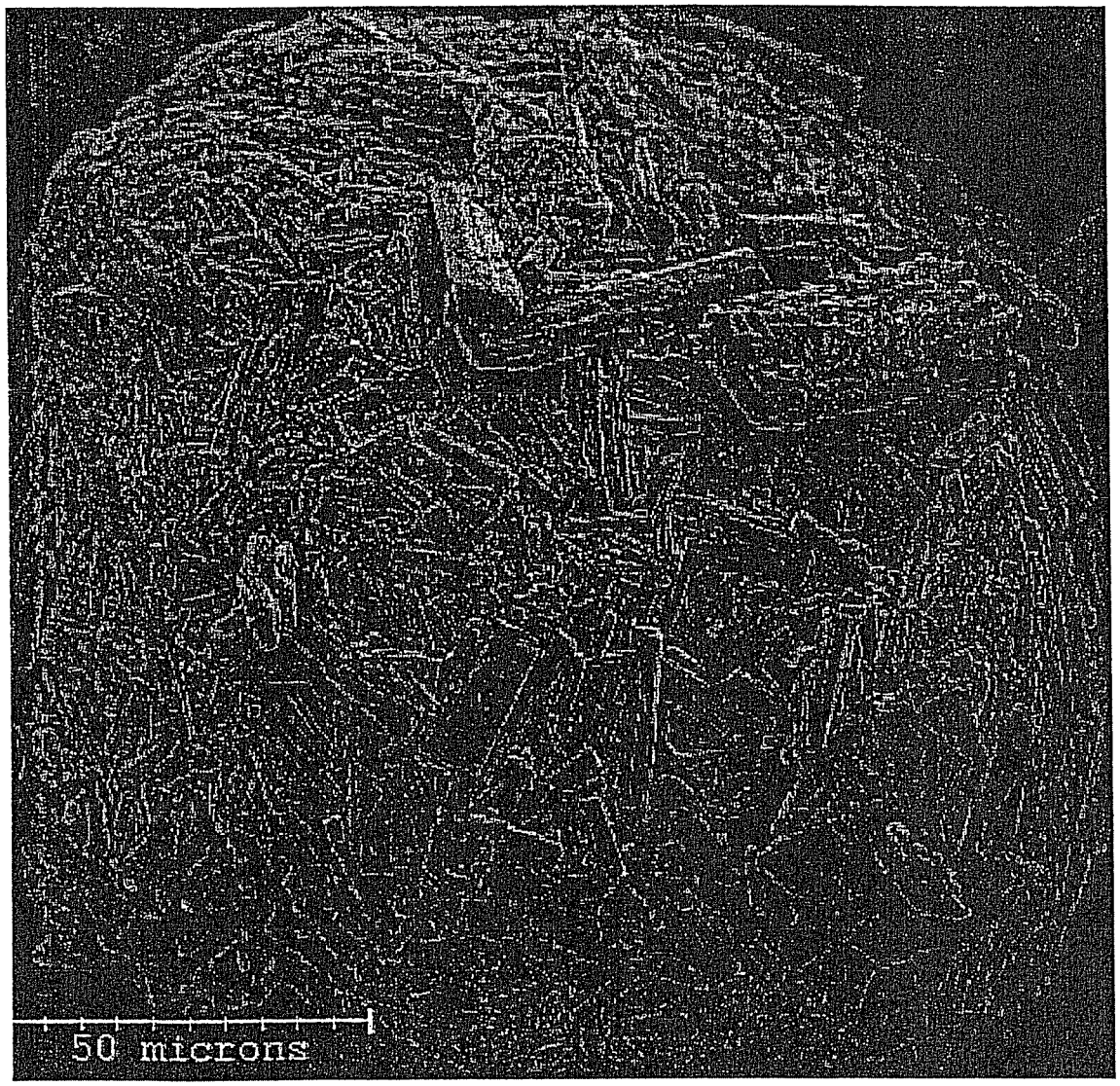
FIG. 1 is an SEM image of a dry granulate particle produced in accordance with the present invention.

The present invention provides a rapidly disintegrating tablet comprising a beneficial ingredient; a directly compressible, water soluble carbohydrate; and a directly compressible, water insoluble filler. Preferably, the tablet of the present invention has a friability of at most about 1.5% and a porosity of from about 15% to about 45%, e.g., from about 15% to about 35%, from about 15% to about 25%, from about 20% to about 35% (e.g., from about 21% to about 32%), from about 20% to about 30%, or from about 20% to about 25% (e.g., from about 21% to about 23%). Preferably, the disintegration time of the tablet of the present invention is within about 120 seconds or less.

The term "rapidly disintegrating" or "rapidly disintegrable" as used herein refers to the ability of a tablet (e.g., a tablet for oral administration) to disintegrate rapidly when contacted with a fluid, particularly an aqueous fluid (e.g., water, bodily fluids (e.g., saliva), and the like), to form a suspension, slurry or dispersion, which facilitates administration of the contents of the tablet (e.g., by forming a suspension, slurry or dispersion, which is easily swallowed).

In a preferred embodiment, the tablet of the present invention is an orally disintegrating tablet, which disintegrates rapidly when contacted with an aqueous fluid (e.g., water or saliva), to form a suspension, slurry or dispersion, which can be easily swallowed. The orally disintegrating tablet of the present invention preferably disintegrates rapidly in the oral cavity when contacted with saliva, to form a suspension, slurry or dispersion, which can be easily swallowed. In one embodiment, the tablet of the present invention is a taste-masked orally disintegrating tablet (e.g. a rapidly disintegrating tablet as described herein, which includes a taste-making agent, an osmotic agent, and the like, or a combination thereof). The term "oral cavity" includes the region within the interior of the mouth, including, but not limited to, the buccal cavity (e.g., anterior to the teeth and gums) as well as the sublingual and supralingual spaces, and the like.

The tablet of the present invention preferably disintegrates within about 120 seconds or less, when contacted with an aqueous fluid (e.g., water, saliva, or a buffered solution), to form a slurry, a dispersion or a suspension, which can be administered (e.g., swallowed) easily. The disintegration time of the tablet of the present invention can range from within about 2 seconds to within about 120 seconds, e.g., from within about 2 seconds to within about 60 seconds, or from within about 2 seconds to within about 30 seconds, as measured by the Standard USP Disintegration Test for Sublingual Tablets. The tablet of the present invention more preferably disintegrates from within about 2 seconds to within about 30 seconds, and still more preferably from within about 2 seconds to within about 20 seconds, and most preferably from within about 2 seconds to within about 10 seconds (e.g., from within about 5 seconds to within about 10 seconds, or from within about 5 seconds to within about 8 seconds), as measured by the Standard USP Disintegration Test for Sublingual Tablets.

When the tablet of the present invention is an orally disintegrating tablet, it preferably can disintegrate completely in the oral cavity within about 120 seconds, and more preferably from within about 2 seconds to within about 120 seconds (e.g., from within about 2 seconds to within about 60 seconds, or from within about 2 seconds to within about 30 seconds), when contacted with saliva, to form a slurry, a dispersion or a suspension, which can be swallowed easily. The orally disintegrating tablet of the present invention most preferably disintegrates completely in the oral cavity from within about 2 seconds to within about 20 seconds, when contacted with saliva, to form a slurry, a dispersion or a suspension, which can be swallowed easily.

The tablet of the present invention can be used as a delivery system for the administration of one or more beneficial ingredients. Any suitable beneficial ingredient can be used in accordance with the present invention. Suitable beneficial ingredients can include, for example, pharmaceutically active agents, nutraceutically active agents, breath fresheners (e.g., mints, such as peppermint, spearmint, etc.), confectionary products (e.g., candy, flavored products, etc.), and the like, and combinations thereof.

Pharmaceutically active agents can include, for example, medicaments or drugs, e.g., analgesics, anti-inflammatory agents, anthelmintics, anti-arrhythmic agents, antibiotics, anticoagulants, antidepressants, antidiabetic agents, antidiarrheal agents, antiemetic agents, antiepileptics, antihistamines, antihypertensive agents, antimuscarinic agents, antimycobacterial agents, antineoplastic agents, immunosuppressants, antithyroid agents, anti-tussive agents, antiviral agents, anxiolytic sedatives, astringents, beta-adrenoceptor blocking agents, cardiac inotropic agents, corticosteroids, cough suppressants, diagnostic agents, diagnostic imaging agents, diuretics, dopaminergics, haemostatics, immuriological agents, lipid regulating agents, muscle relaxants, parasympathomimetics, parathyroid calcitonin and biphosphonates, prostaglandins, radio-pharmaceuticals, steroids, anti-allergic agents, stimulants and anoretics, sympathomimetics, thyroid agents, vasodilators, xanthines, and the like, and mixtures thereof. Exemplary pharmaceutically active agents include, e.g., mirtazapine, olanzapine, ondansetron, NSAIDs, acetaminophen, enalapril, famotidine, fluoxetine, lorazepam, loperamide, loratidine, narcotic analgesics, e.g., morphine, hydrocodone, and the like, oxazepam, piroxicam, rizatriptan, zolmitriptan, zolpidem, hyoscyamine and salts thereof, e.g., hyoscyamine sulfate, and the like.

Nutraceutically active agents can include, for example, dietary supplements, minerals, vitamins, and the like, and combinations thereof. Exemplary nutraceutically active agents include, e.g., vitamin A, vitamin D, vitamin E (e.g., d-α-tocopherol, d-α-tocopheryl acetate, dl-α-tocopherol and dl-α-tocopheryl acetate), vitamin B1 and derivatives thereof, vitamin B2 and derivatives thereof, vitamin B6 and derivatives thereof (e.g., pyridoxine hydrochloride), vitamin C and derivatives thereof (e.g., ascorbic acid, sodium L-ascorbate, etc.), vitamin B12 and derivatives thereof, fluoride (e.g., sodium fluoride), calcium, magnesium, iron, proteins, amino acids, oligosaccharides, and the like, and mixtures thereof. It will be appreciated that there may be circumstances in which a pharmaceutically active agent also may function as a nutraceutically active agent, and in which a nutraceutically active agent also may function as a pharmaceutically active agent.

Beneficial ingredients also can include, for example, detergents, foaming agents, anti-foaming agents, agriculturally beneficial products (e.g., fertilizers, pesticides, antimicrobial agents, herbicides, etc.), and the like, and combinations thereof. It will be appreciated that the beneficial agent also can include one or more of the additional ingredients in the tablet of the present invention, e.g., the directly compressible, water soluble carbohydrate, the directly compressible, water insoluble filler, and the like.

The tablet of the present invention can include any suitable amount of the beneficial agent, which is preferably an effective amount. When the beneficial agent is a pharmaceutically active agent, the effective amount of the pharmaceutically active agent preferably is a therapeutically or pharmaceutically effective amount. When the beneficial agent is a nutraceutically active agent, the effective amount of the nutraceutically active agent preferably is a nutraceutically effective amount. Any suitable dosage level of a pharmaceutically active agent or a nutraceutically active can be employed in the tablet of the present invention. The dose to be administered to an animal, particularly a human, in accordance with the present invention should be sufficient to effect a prophylactic or therapeutic response in the animal over a reasonable time frame. One skilled in the art will recognize that the amount of active ingredient will vary depending upon a variety of factors including, for example, the activity of the specific compound employed; the age, body weight, general health, sex, and diet of a particular patient or patient population; the time of administration, rate of absorption, and rate of excretion; the potential interactions with other drugs taken separately or in combination; and the severity of the particular disease or condition for which a therapeutic effect is desired. The size of the dose will also be determined by the existence, nature, and extent of any adverse side effects that might accompany the administration of a particular compound. Other factors, which affect the specific dosage, include, for example, bioavailability, metabolic profile, and the pharmacodynamics associated with the particular compound to be administered in a particular patient.

For example, a pharmaceutically effective amount can include the amount or quantity of a pharmaceutically active agent, which is sufficient to elicit the required or desired therapeutic response, e.g., an amount, which is sufficient to elicit a biological or therapeutic response when administered to a patient. A nutraceutically effective amount can include an amount or quantity of a nutraceutically active agent, which is sufficient to elicit a nutritive response when administered to a patient. A nutraceutically effective amount can include, for example, an amount that constitutes at least about 10% of the United States Recommended Daily Allowance ("RDA") of a particular nutraceutical ingredient for a patient. For a mineral or vitamin, for example, a nutraceutically effective amount also can include as much as about 100% or more of the applicable RDA.

The amount of active ingredient in the tablet of the present invention also can be expressed in terms of a weight percentage. For example, the active ingredient in the tablet of the present invention can constitute from greater than 0% to about 80% by weight based on the total weight of the tablet, or from greater than 0% to about 60% by weight based on the total weight of the tablet. The amount of active ingredient in the tablet of the present invention also can be expressed in terms of total mass per tablet. For example, the tablet of the present invention can include an active ingredient in an amount of from about 1 µg to about 2 g per tablet, or from about 0.01 mg and about 1000 mg per tablet. For example, the tablets of the present invention can include one or more active ingredients in amounts that range, e.g., from about 0.1 mg to about 0.5 mg, from about 1 mg to about 20 mg (e.g., 2 mg, 8 mg, 15 mg), from about 50 mg to about 100 mg (e.g., 80 mg), from about 100 mg to about 500 mg (e.g., 100 mg, 200 mg, 250 mg, 300 mg), or from about 500 mg to about 1000 mg.

Directly compressible excipients are well known in the art, and have been characterized by their ability to bond to other materials to form a strong compact. Any suitable directly compressible, water soluble carbohydrate can be used in the tablet of the present invention. Suitable directly compressible, water soluble carbohydrates can include, for example, directly compressible, water soluble sugars and directly compressible, water soluble sugar alcohols.

Preferred directly compressible, water soluble carbohydrates include, for example, directly compressible mannitol, directly compressible sorbitol, directly compressible maltitol, directly compressible lactose, directly compressible sucrose, directly compressible xylose, directly compressible trehalose, directly compressible dextrose, and the like, and combinations thereof. Preferred directly compressible, water soluble carbohydrates include directly compressible mannitol, which is preferably a directly compressible spray dried mannitol. The tablet of the present invention most preferably comprises a directly compressible granulate obtained by wet granulation of a directly compressible spray dried mannitol. The directly compressible granulate preferably is obtained by wet granulation of a directly compressible spray dried mannitol in the presence of a solution, dispersion or slurry comprising a solvent, and more preferably is obtained by wet granulation of a directly compressible spray dried mannitol in the presence of a solution, dispersion or slurry comprising the active ingredient and a solvent. In a preferred embodiment, the directly compressible granulate is obtained by wet granulation of a directly compressible spray dried mannitol in the presence of the active ingredient and an aqueous solvent, which aqueous solvent is most preferably water.

The wet granulation can be performed by adding a granulating solvent to a dry mixture of a directly compressible, water soluble carbohydrate and a beneficial ingredient, and granulating the resulting composition. Alternatively, the wet granulation can be performed by adding a granulation solvent, which is a solution, slurry or dispersion of a beneficial ingredient and a solvent, to a directly compressible, water soluble carbohydrate, and granulating the resulting composition. In a particularly preferred embodiment, the solvent is aqueous (e.g., water) and the water soluble carbohydrate is a spray-dried mannitol. For example, the directly compressible granulate can be obtained by adding a solution, slurry or dispersion of a beneficial agent and water, to a directly compressible spray dried mannitol, and granulating the resulting composition. Alternatively, the directly compressible granulate can be obtained by adding water, to a dry mixture of a directly compressible spray dried mannitol and a beneficial ingredient, and granulating the resulting composition.

When a directly compressible spray-dried mannitol is used in the tablet of the present invention, the directly compressible spray-dried mannitol preferably comprises crystalline particles having a substantially rounded shape. It is further preferred that, when a directly compressible spray dried mannitol is used, the directly compressible spray dried mannitol comprises particles having a diameter of from about 20 µm to about 200 µm, and more preferably from about 50 µm to about 175 µm, and still more preferably from about 75 µm to about 150 µm. In a preferred embodiment, the directly compressible spray-dried mannitol comprises crystalline mannitol particles having a substantially rounded shape, wherein about 40% to about 80% of the spray dried mannitol particles have a diameter of from about 20 µm to about 200 µm. In a particularly preferred embodiment, the directly compressible spray-dried mannitol comprises crystalline mannitol particles having a substantially rounded shape, wherein about 60% of the particles of the spray dried mannitol have a diameter of from about 75 µm to about 150 µm.

The directly compressible, water soluble carbohydrate can be present in the tablet of the present invention in any suitable amount, e.g., in an amount of from about 1% by weight to about 99% by weight based on the total weight of the tablet. Preferably, the directly compressible, water soluble carbohydrate is present in an amount of from about 30% by weight to about 95% by weight based on the total weight of the tablet, and more preferably from about 60% by weight to about 85% by weight based on the total weight of the tablet.

Any suitable directly compressible, water insoluble filler can be used in accordance with the present invention. Suitable directly compressible, water insoluble fillers can include, for example, directly compressible water insoluble celluloses (e.g., microcrystalline cellulose), directly compressible water insoluble cellulose derivatives (e.g., ethyl cellulose), and the like. Preferably, the directly compressible, water insoluble filler is a directly compressible, water insoluble cellulose, which is most preferably microcrystalline cellulose. A preferred directly compressible microcrystalline cellulose, which can be used in accordance with the present invention, has a bulk density of from about 0.2 g/cm3 to about 0.4 g/cm3, e.g., about 0.3 g/cm3. The mean particle size of the directly compressible microcrystalline cellulose used in accordance with the present invention preferably is from about 20 µm to about 200 µm.

The directly compressible, water insoluble filler can be present in the tablet of the present invention in any suitable amount, e.g., in an amount of from about 1% by weight to about 40% by weight based on the total weight of the tablet. Preferably, the directly compressible, water insoluble filler is present in an amount of from about 10% by weight to about 30% by weight based on the total weight of the tablet, and is more preferably present in an amount of from about 15% by weight to about 20% by weight based on the total weight of the tablet.

The friability of the tablet of the present invention preferably is at most about 1.5%, but is more preferably at most about 1%, and is most preferably at most about 0.5% (e.g., about 0.1% or about 0.2%).

Hardness refers to the diametral breaking strength as measured by conventional pharmaceutical tablet hardness determination methods, which are well known in the art. A higher hardness value, sometimes measured in Newtons (N), generally is indicative of a higher diametral strength. The hardness of the tablet of the present invention preferably ranges from about 10 N to about 47 N, and more preferably from about 14 N to about 35 N, and most preferably from about 21 N to about 28 N.

The term "porosity" is used herein as a measurement, which is indicative of the amount of internal void space remaining in the tablet after compression, and is measured as a percentage of the pore volume (or void space) relative to the total tablet volume. The porosity of the tablet of the present invention preferably is from about 15% to about 45%, e.g., from about 15% to about 35%, from about 15% to about 25%, from about 20% to about 35% (e.g., from about 21% to about 32%), from about 20% to about 30%, or from about 20% to about 25% (e.g., from about 21% to about 23%). The porosity of the tablet of the present invention is believed to be relatively high as compared to other conventional compressed rapidly disintegrating tablets. The high porosity of the tablet of the present invention is believed to promote rapid disintegration upon contact with saliva in the oral cavity, to form a suspension, slurry or dispersion, which can be swallowed easily without water or mastication.

The tablet of the present invention can have any suitable exterior surface area, e.g., from about 0.10 square inches to about 2.0 square inches, e.g., from about 0.1 square inches to about 1.0 square inches, from about 0.1 square inches to about 0.5 square inches, from about 0.1 square inches to about 0.3 square inches, from about 0.1 to about 0.2 square inches. Preferably, the tablet of the present invention has an exterior surface area of from about 0.30 square inches to about 1.0 square inches (e.g., from about 0.50 square inches to about 1.0 square inches), and more preferably has an exterior surface area of from about 0.50 square inches to about 0.80 square inches. The tablet of the present invention also can have any suitable density, which is a measure of mass per unit volume and is expressed in terms of grams per milliliter (g/mL). The density of the composition can range from about 0.5 g/mL to about 2.5 g/mL, but is preferably from about 0.7 g/mL to about 2.0 g/mL, and is more preferably from about 0.7 g/mL to about 1.5 g/mL (e.g., from about 1.1 g/mL to about 1.5 g/mL (e.g., from 1.1 g/mL to 1.3 g/mL)).

The tablet of the present invention preferably includes one or more additional ingredients selected from the group consisting of disintegrants, lubricants, water soluble fillers, water insoluble fillers, and the like, and combinations thereof. The tablet of the present invention optionally can include surface active agents, taste masking agents, flavorants, sweeteners, colorants, and the like, and combinations thereof.

Suitable disintegrants can include, for example, microcrystalline cellulose, sodium carboxymethyl cellulose, calcium carboxymethyl cellulose, modified cellulose gum, crospovidone, alginic acid and alginates, pregelatinized starch, sodium starch glycollate, modified corn starch, starch (e.g. potato/maize starch), and the like, and combinations thereof.

Suitable surface active agents can include, for example, sodium dodecyl sulfate, sodium lauryl sulfate, polyoxyethylene sorbitan fatty acid esters (Tweens), polyoxyethylene stearates, sorbitan fatty acid esters (Spans), and the like, and combinations thereof.

Suitable lubricants can include, for example, stearates (e.g. stearic acid, magnesium stearate, zinc stearate, calcium stearate, and the like), talc, polyethylene glycol, liquid paraffin, sodium lauryl sulfate, magnesium lauryl sulfate, colloidal silicon dioxide, palmitostearate, vegetable oil, hydrogenated vegetable oil, and the like, and combinations thereof.

Suitable fillers can include, for example, lactose, granular sugars, confectioners sugar, dextrose, mannitol, sorbitol, xylitol, calcium carbonate, magnesium carbonate, calcium phosphate, calcium sulfate, microcrystalline cellulose, powdered cellulose, pregelatinized starch, starch, magnesium trisilicate, aluminum hydroxide, and the like, and combinations thereof.

Suitable flavorants can include, for example, flavors, which are known to those of skill in the art, such as, for example, natural flavors, artificial flavors, and combinations thereof. Flavorants may be chosen, e.g., from synthetic flavor oils and flavoring aromatics and/or oils, oleoresins, extracts derived from plants, leaves, flowers, fruits, and the like, and combinations thereof. Non-limiting examples of flavor oils include spearmint oil, cinnamon oil, oil of wintergreen (methyl salicylate), peppermint oil, clove oil, bay oil, anise oil, eucalyptus oil, thyme oil, cedar leaf oil, oil of nutmeg, allspice, oil of sage, mace, oil of bitter almonds, and cassia oil. Suitable flavoring agents also include, for example, artificial, natural and synthetic fruit flavors such as vanilla, citrus oils (e.g., lemon, orange, lime, and grapefruit), and fruit essences (e.g., apple, pear, peach, grape, strawberry, raspberry, cherry, plum, pineapple, and apricot), and the like, and combinations thereof. The flavoring agents may be used in liquid or solid form and, as indicated above, may be used individually or in admixture. Other flavorants can include, for example, certain aldehydes and esters, e.g., cinnamyl acetate, cinnamaldehyde, citral diethylacetal, dihydrocarvyl acetate, eugenyl formate, p-methylamisol, and the like, and combinations thereof.

Suitable sweeteners can include, for example, solid natural or synthetic sweeteners, e.g., amino acid and dipeptide based sweeteners, e.g., glycerrhizin, saccharin and its salts, aspartame, and the like, and combinations thereof.

Suitable colorants can include, for example, red, black and yellow iron oxides; FD & C dyes (e.g., FD & C blue No. 2, FD & C red No. 40); and the like, and combinations thereof.

The present invention further provides a process for producing a rapidly disintegrating tablet, which method includes: (i) wet-granulating a directly compressible, water soluble carbohydrate and a directly compressible, water insoluble filler in the presence of a beneficial ingredient and a solvent, to produce a wet granulate comprising the beneficial ingredient, the directly compressible, water soluble carbohydrate and the directly compressible, water insoluble filler; (ii) drying the wet granulate, to produce a dry granulate; (iii) adding one or more ingredients selected from the group consisting of disintegrants, lubricants, water soluble fillers, water insoluble fillers, and the like, and combinations thereof; (iv) optionally adding one or more ingredients selected from the group consisting of surface active agents, flavorants, sweeteners, colorants, and the like, and combinations thereof; and, (v) compressing, to form the tablet. Suitable directly compressible, water soluble carbohydrates include the directly compressible, water soluble carbohydrates as described herein. Directly compressible, water soluble carbohydrate can include, for example, directly compressible mannitol, directly compressible sorbitol, directly compressible maltitol, directly compressible lactose, directly compressible sucrose, directly compressible xylose, directly compressible trehalose, directly compressible dextrose, and combinations thereof.

Preferably, the directly compressible, water soluble carbohydrate is directly compressible mannitol, e.g., directly compressible spray dried mannitol as described herein. For example, when a directly compressible spray-dried mannitol is used, the directly compressible spray dried mannitol may comprise particles having a diameter of from about 20 µm to about 200 µm, e.g., from about 50 µm to about 175 µm, or from about 75 µm to about 150 µm. The spray dried mannitol can comprise crystalline mannitol particles having a substantially rounded shape, wherein about 40% to about 80% of the spray dried mannitol particles have a diameter of from about 20 µm to about 200 µm. In a particularly preferred embodiment, the directly compressible, spray-dried mannitol comprises crystalline mannitol particles having a substantially rounded shape, wherein about 60% of the particles of the spray dried mannitol have a diameter of from about 75 μm to about 150 μm.

Preferably the water insoluble filler is a directly compressible polysaccharide as described herein. For example, the directly compressible polysaccharide can include a directly compressible, water insoluble cellulose, e.g., microcrystalline cellulose. The directly compressible microcrystalline cellulose can have a bulk density, e.g., of from about 0.2 g/cm3 to about 0.4 g/cm3, e.g., about 0.3 g/cm3. The mean particle size of the directly compressible microcrystalline cellulose used in accordance with the present invention can be from about 20 μm to about 200 μm.

The granulating solvent, which can be used for carrying out the wet granulation step in accordance with the method of the present invention, can be any suitable solvent, but is preferably an aqueous solvent, such as water or a mixture of water and another solvent. Most preferably, the granulating solvent is water. In a particularly preferred embodiment, the directly compressible granulate is prepared by wet granulating a mixture comprising a directly compressible, water soluble carbohydrate; a directly compressible, water insoluble filler, and, as a granulation solvent, a solution, dispersion or slurry of a beneficial ingredient in water. In another particularly preferred embodiment, the wet granulate is prepared by adding water as a granulation solvent to a mixture comprising a directly compressible, water soluble carbohydrate; a directly compressible, water insoluble filler; and a beneficial ingredient, and granulating the resulting composition.

The shape and size of the tablet of the present invention is not limited to any particular shape or size. Examples of suitable shapes include triangle, square, round, cylinder, animal-shape, irregular shape (Caplet-type), ring (donut shape), flat-faced tablet, biconvex tablet, multi-layer tablet, and the like. In addition, letters or characters may be debossed or embossed on the tablet.

The following examples further illustrate the invention but, of course, should not be construed as in any way limiting its scope.

EXAMPLE 1

This example describes a process for producing a rapidly disintegrating tablet of the present invention.

Hyoscyamine sulfate (0.188 kg) is added to 2.0 kg of Purified Water, USP, in a stainless steel container. An additional 1.0 kg of Purified Water, USP, is added to rinse the remaining hyoscyamine suflate, and the rinse solution is added to the solution in the stainless steel container to form a concentrated hyoscyamine solution. The concentrated hyoscyamine solution is transferred, with slow addition, to a stainless steel mixing tank containing 15.0 kg of Purified Water, USP. The stainless steel mixing tank is equipped with a mixer, and the resulting diluted hyoscyamine solution is mixed slowly for 15 minutes. The container used to prepare the concentrated hyoscyamine solution is rinsed with an additional 1.0 kg of Purified Water, USP, and the rinse solution is added to the stainless steel mixing tank containing the mixed diluted hyoscyamine solution.

Microcrystalline Cellulose NF (20.0 kg) and Mannitol, USP (Spray-Dried, 69.1 kg, Mannogem™ EZ from SPI Pharma Group) are loaded into a Diosna P400 High Shear Granulator with an inner bowl diameter of 43.25 inches, an impeller radius of 20.75 inches, and a hub-to-tip length of 16.75 inches. The Diosna P400 High Shear Mixer is equipped with a "4040" spray nozzle on the Diosna liquid inlet. The ingredients in the Diosna P400 are dry mixed for 3 minutes at an impeller speed of 100 rpm and a chopper speed of 1400 rpm.

The wet granulation process is performed by pumping the diluted hyoscyamine solution into the Diosna P400 granulator using the Diosna pump, set at 30%, with an addition time of 4 minutes. The wet material is granulated at an impeller speed of 100 rpm and a chopper speed of 1400 rpm for an additional 1 minute or until the mixer load reaches 28%. The tank used to mix the diluted hyoscyamine solution is rinsed with an additional 6.0 kg of Purified Water, USP, and the rinse solution is pumped into the Diosna P400 granulator using the Diosna pump, set at 30%, with an addition time of 1.25 minutes or until the mixer load reaches 28%. The wet material is mixed at an impeller speed of 100 rpm and a chopper speed of 1400 rpm until the Mixer Load of the Diosna P400 is 33% (40 minutes maximum), to form a wet granulate.

The wet granulate is placed in an Aeromatic Fluid Bed Dryer, and the material is dried at an inlet air temperature of 55±3° C. for 45-90 minutes (i.e., until the weight loss on drying is not greater than 1% using a Mettler moisture analyzer). The dry granulate is then fluidized with ambient air until it reaches room temperature, to produce a cooled, dry granulate, an exemplary SEM image of which is shown in FIG. 1. The cooled, dry granulate is sized using a Fitzmill, fitted with a #2 screen (hole diameter of 0.065 inches), at medium speed with knives forward.

The dry, sized granulate containing hyoscyamine sulfate is passed through a Sweco Separator equipped with an 18-mesh screen and placed into a polyethylene lined container. Separately, two portions of Mannitol, USP (Spray-Dried), weighing 20.0 kg and 21.5 kg, are passed through the Sweco Separator equipped with an 18-mesh screen, and placed into two polyethylene-lined containers. Microcrystalline Cellulose NF (7.0 kg), Aspartame NF (1.35 kg), Silicon Dioxide Colloidal NF (0.375 kg), Peppermint Flavor (1.5 kg), and Crospovidone NF (9.0 kg) are passed through the Sweco Separator equipped with an 18-mesh screen, and combined into a polyethylene-lined container.

The screened 20.0-kg portion of Mannitol, USP (Spray-Dried), is transferred into a Twin Shell Blender, and the screened dry granulate containing hyoscyamine sulfate is thereafter transferred to the Twin Shell Blender. Next, the screened Microcrystalline Cellulose NF, Aspartame NF, Silicon Dioxide Colloidal NF, Peppermint Flavor, and Crospovidone NF mixture is transferred to the Twin Shell Blender, and the screened 21.5-kg portion of Mannitol, USP (Spray-Dried) is thereafter transferred to the Twin Shell Blender. The resulting mixture is dry blended for 10 minutes. Magnesium Stearate NF is added to lubricate the resulting blend, and the blend is mixed for an additional 3 minutes. The lubricated blend is compressed using a Double Sided Rotary Tablet Press into 0.250 inch round, flat-faced tablets.

Table 1 illustrates the physical characteristics of tablets produced in accordance with this example.

TABLE 1

| Batch | Average Hardness (N) | Average Density (g/cm3) | Average Porosity | Average Friability (% loss in 4 minutes) | Disintegration Time (seconds) |
|---|---|---|---|---|---|
| 1 | 23.0 | 1.259 | 23.232% | 0.17 | 5-7 |
| 2 | 25.0 | 1.105 | 21.1227% | 0.17 | 5 |
| 3 | 24.0 | 1.167 | 21.4785% | 0.11 | 8 |

The thickness of the tablets prepared according to this example typically ranges from 0.105 inches to 0.122 inches. The external surface area of the tablets prepared according to this example typically averages about 0.175 square inches per tablet.

EXAMPLE 2

This example describes a process for producing a rapidly disintegrating tablet of the present invention. Following the procedure as described in Example 1, the tablets are prepared using the ingredients listed in Table 2.

TABLE 2

| Ingredients | Amount per Tablet (mg) |
| --- | --- |
| Hyoscyamine sulfate | 0.125 |
| Spray-dried mannitol (Mannogem ™ EZ, SPI Pharma) | 73.725 |
| Microcrystalline cellulose | 18.0 |
| Aspartame | 0.9 |
| Colloidal silicon dioxide | 0.25 |
| Peppermint flavor | 1.0 |
| Crospovidone | 6.0 |
| Magnesium stearate | 2.0 |

EXAMPLE 3

This example describes a process for producing a rapidly disintegrating tablet of the present invention. Following the procedure as described in Example 1, the tablets are prepared using the ingredients listed in Table 3.

TABLE 3

| Ingredients | Amount per Tablet (mg) |
| --- | --- |
| Sodium Fluoride | 2.21 |
| Spray-dried mannitol (Mannogem ™, SPI Pharma) | 69.24 |
| Microcrystalline cellulose | 18.0 |
| Citric Acid | 1.1 |
| Aspartame | 0.9 |
| Colloidal silicon dioxide | 0.25 |
| Imitation black cherry flavor | 2.087 |
| Crospovidone | 4.0 |
| Magnesium stearate | 2.0 |
| Red Iron Oxide (SICOPHARM Red 30 Iron Oxide) | 0.213 |

EXAMPLE 4

This example describes a process for producing a rapidly disintegrating tablet of the present invention.

Mannitol, USP (Spray-Dried, Mannogem™ EZ from SPI Pharma Group, 103.9 kg), Sodium Fluoride, USP (45.25% fluoride, 3.315 kg), and Red Iron Oxide (SICOPHARM Red 30 Iron Oxide, 0.320 kg) are loaded into a Diosna P400 High Shear Granulator with an inner bowl diameter of 43.25 inches, an impeller radius of 20.75 inches, and a hub-to-tip length of 16.75 inches. The Diosna P400 High Shear Mixer is equipped with a "4040" spray nozzle on the Diosna liquid inlet. The ingredients in the Diosna P400 are dry mixed for 5 minutes at an impeller speed of 100 rpm and a chopper speed of 1400 rpm.

The wet granulation process is performed by pumping purified water, USP, into the Diosna P400 granulator using the Diosna pump, set at 30%, with an addition time of 4 minutes. The wet material is granulated at an impeller speed of 100 rpm and a chopper speed of 1400 rpm for an additional 1 minute or until the mixer load reaches 28%. Additional purified water, USP, is pumped into the Diosna P400 granulator using the Diosna pump, set at 30%. The wet material is mixed at an impeller speed of 100 rpm and a chopper speed of 1400 rpm until the Mixer Load of the Diosna P400 is 31% (20 minutes maximum), to form a wet granulate.

The wet granulate is placed in an Aeromatic Fluid Bed Dryer, and the material is dried at an inlet air temperature of 55±3° C. for 60-90 minutes (i.e., until the weight loss on drying is not greater than 1% using a Mettler moisture analyzer). The dry granulate is then fluidized with ambient air until it reaches room temperature, to produce a cooled, dry granulate. The cooled, dry granulate is sized using a Fitzmill, fitted with a #2 screen (hole diameter of 0.065 inches), at medium speed with knives forward.

The dry, sized granulate containing sodium fluoride is passed through a Sweco Separator equipped with an 18-mesh screen, divided into two equal portions, and placed into two polyethylene lined container. Microcrystalline Cellulose NF (27.0 kg), Aspartame NF (1.35 kg), Silicon Dioxide Colloidal NF (0.375 kg), Citric Acid USP Anhydrous (1.65 kg), Black Cherry Flavor (Delco #379023, 3.131 kg), and Crospovidone NF (6.0 kg) are passed through the Sweco Separator equipped with an 18-mesh screen, and combined into a polyethylene-lined container.

The screened dry granulate containing sodium fluoride (one portion) is transferred to a Twin Shell Blender. Next, the screened Microcrystalline Cellulose NF, Aspartame NF, Silicon Dioxide Colloidal NF, Citric Acid USP, Black Cherry Flavor, and Crospovidone NF mixture is transferred to the Twin Shell Blender, follow by addition of the second portion of the screened dry granulate containing sodium fluoride, and the resulting mixture is dry blended for 10 minutes. Magnesium Stearate NF is added to lubricate the resulting blend, and the blend is mixed for an additional 3 minutes. The lubricated blend is compressed using a Double Sided Rotary Tablet Press, to provide 0.250 inch round tablets. Tablets prepared according to this process have a friability of from 0.0% to about 1.1% and a disintegration time of about 14-18 seconds.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A process for producing a rapidly disintegrating tablet, wherein the process comprises:
   (i) wet-granulating a mixture comprising a directly compressible, water soluble carbohydrate; a directly compressible, water insoluble filler; a beneficial ingredient; and a solvent, to form a wet granulate;
   (ii) drying the wet granulate, to produce a directly compressible dry granulate;
   (iii) adding one or more ingredients selected from the group consisting of disintegrants, lubricants, water soluble fillers, and water insoluble fillers;
   (iv) optionally adding one or more ingredients selected from the group consisting of surface active agents, flavorants, sweeteners, and colorants; and,
   (v) compressing, to form the tablet, wherein, when contacted with an aqueous fluid, the tablet disintegrates rapidly to form a suspension, slurry or dispersion.

2. The process of claim 1, wherein the tablet has a friability of not more than about 1.5% and a porosity of from about 15% to about 45%.

3. The process of claim 1, wherein the directly compressible, water soluble carbohydrate is directly compressible mannitol, directly compressible sorbitol, directly compressible maltitol, directly compressible lactose, directly compressible sucrose, directly compressible xylose, directly compressible trehalose, directly compressible dextrose, or a combination thereof.

4. The process of claim 1, wherein the directly compressible, water soluble carbohydrate comprises directly compressible mannitol.

5. The process of claim 4, wherein the directly compressible mannitol comprises crystalline particles having a substantially rounded shape.

6. The process of claim 4, wherein the directly compressible mannitol comprises spray dried mannitol.

7. The process of claim 4, wherein the directly compressible mannitol comprises particles having a diameter of from about 75 μm to about 150 μm.

8. The process of claim 7, wherein about 60% of the mannitol particles have a diameter of from about 75 μm to about 150 μm.

9. The process of claim 1, wherein the directly compressible, water insoluble filler is a directly compressible polysaccharide.

10. The process of claim 9, wherein the directly compressible, water insoluble filler is microcrystalline cellulose.

11. The process of claim 1, wherein the solvent is an aqueous solvent.

12. The process of claim 1, wherein the solvent is water.

13. The process of claim 1, wherein (i) comprises wet granulating a mixture comprising a directly compressible, water soluble carbohydrate; a directly compressible, water insoluble filler; the beneficial ingredient; and water, to form the wet granulate.

14. The process of claim 1, wherein the tablet is a round, flat-faced tablet.

15. The process of claim 1, wherein the tablet has a porosity of from about 15% to about 35%.

16. The process of claim 1, wherein the tablet has a porosity of from about 20% to about 30%.

17. The process of claim 1, wherein the tablet disintegrates in from within about 2 seconds to within about 120 seconds.

18. The process of claim 1, wherein the tablet disintegrates in from within about 2 seconds to within about 60 seconds.

19. The process of claim 1, wherein (i) comprises wet-granulating a mixture of directly compressible mannitol; directly compressible microcrystalline cellulose; a beneficial ingredient; and water, to form a wet granulate, and wherein the tablet has a friability of not more than about 1.5% and a porosity of from about 15% to about 45%.

20. The process of claim 19, wherein the directly compressible mannitol comprises crystalline particles having a substantially rounded shape.

21. The process of claim 20, wherein the directly compressible mannitol is spray dried mannitol.

22. The process of claim 20, wherein about 60% of the mannitol particles have a diameter of from about 75 μm to about 150 μm.

23. The process of claim 20, wherein the microcrystalline cellulose has a bulk density of from about 0.2 g/cm$^3$ to about 0.4 g/cm$^3$.

24. The process of claim 23, wherein the microcrystalline cellulose has a mean particle size of from about 20 μm to about 200 μm.

25. The process of claim 20, wherein the tablet has a friability of at most about 1%.

26. The process of claim 20, wherein the tablet has a hardness of from about 10 N to about 47 N.

27. The process of claim 20, wherein the tablet has a hardness of from about 14 N to about 35 N.

28. The process of claim 20, wherein the beneficial ingredient is ondansetron.

* * * * *